United States Patent
Koerber et al.

(10) Patent No.: US 11,440,861 B2
(45) Date of Patent: Sep. 13, 2022

(54) PROCESS FOR PREPARATION OF 5-BROMO-1,3-DICHLORO-2-FLUORO-BENZENE

(71) Applicant: BASF SE, Ludwigshafen (DE)

(72) Inventors: Karsten Koerber, Ludwigshafen (DE); Michael Rack, Ludwigshafen (DE); Pascal Bindschaedler, Winterthur (CH); Martin John McLaughlin, Ludwigshafen (DE); Birgit Gockel, Ludwigshafen (DE); Devendra Vyas, Research Triangle Park, NC (US); Sebastian Soergel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 17/295,102

(22) PCT Filed: Nov. 25, 2019

(86) PCT No.: PCT/EP2019/082352
§ 371 (c)(1),
(2) Date: May 19, 2021

(87) PCT Pub. No.: WO2020/114813
PCT Pub. Date: Jun. 11, 2020

(65) Prior Publication Data
US 2022/0017439 A1 Jan. 20, 2022

(30) Foreign Application Priority Data
Dec. 4, 2018 (EP) .................................. 18209956

(51) Int. Cl.
| | |
|---|---|
| *C07C 17/35* | (2006.01) |
| *B01J 21/18* | (2006.01) |
| *B01J 23/44* | (2006.01) |
| *C07C 25/08* | (2006.01) |
| *C07C 245/20* | (2006.01) |
| *C07C 37/045* | (2006.01) |
| *C07C 39/30* | (2006.01) |
| *C07C 17/093* | (2006.01) |

(52) U.S. Cl.
CPC .............. *C07C 17/35* (2013.01); *B01J 21/18* (2013.01); *B01J 23/44* (2013.01); *C07C 17/093* (2013.01); *C07C 25/08* (2013.01); *C07C 37/045* (2013.01); *C07C 39/30* (2013.01); *C07C 245/20* (2013.01)

(58) Field of Classification Search
CPC ..... C07C 17/35; C07C 17/093; C07C 245/20; C07C 37/045; C07C 39/30; B01J 21/18; B01J 23/44
See application file for complete search history.

(56) References Cited

FOREIGN PATENT DOCUMENTS

| | | |
|---|---|---|
| CN | 103664511 A | 3/2014 |
| EP | 1731512 A1 | 12/2006 |
| WO | WO-2005/080343 A2 | 9/2005 |
| WO | WO-2009/080250 A2 | 7/2009 |
| WO | WO-2010/020522 A1 | 2/2010 |
| WO | WO-2010/149506 A1 | 12/2010 |
| WO | WO-2011/067272 A1 | 6/2011 |
| WO | WO-2012/007426 A1 | 1/2012 |
| WO | WO-2012/163959 A1 | 12/2012 |
| WO | WO-2013/026929 A1 | 2/2013 |
| WO | WO-2016/058895 A1 | 4/2016 |
| WO | WO-2016/102482 A1 | 6/2016 |

OTHER PUBLICATIONS

Atkinson, et al., "dl-4,4',6,6'-Tetrachlorodiphenic Acid", Organic Syntheses, vol. 31, 1951, 4 pages.
European Search Report for EP Patent Application No. 18209956.4, dated May 13, 2019, 3 pages.
Evans, D. F., et al. "Studies on Grignard reagents. Part I. Fluorine nuclear magnetic resonance spectra of fluoroaryl Grignard reagents." *Journal of the Chemical Society A: Inorganic, Physical, Theoretical* (1967): 1643-1648.
International Application No. PCT/EP2019/082352, International Search Report and Written Opinion, dated Jan. 27, 2020.

*Primary Examiner* — Jafar F Parsa
(74) *Attorney, Agent, or Firm* — Marshall, Gerstein & Borun LLP

(57) ABSTRACT

The invention relates to a process for the preparation of 5-bromo-1,3-dichloro-2-fluoro-benzene by diazotization and reduction of 6-bromo-2,4-dichloro-3-fluoro-aniline, which is obtained by bromination of 2,4-dichloro-3-fluoro-aniline, which is obtained by reduction of 1,3-dichloro-2-fluoro-4-nitro-benzene, and a process for preparing active compounds of formula V (Formula V) wherein the variables are defined in the specification by further transforming 5-bromo-1,3-dichloro-2-fluoro-benzene obtained from 2,4-dichloro-3-fluoro-aniline by the process according to the invention.

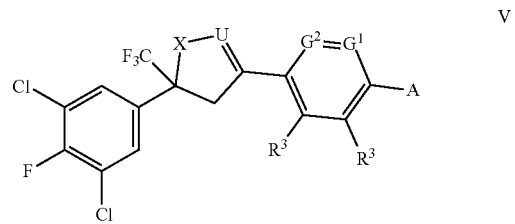

12 Claims, No Drawings

PROCESS FOR PREPARATION OF 5-BROMO-1,3-DICHLORO-2-FLUORO-BENZENE

CROSS-REFERENCE TO RELATED APPLICATIONS

This is the U.S. national phase of International Application No. PCT/EP2019/082352, filed Nov. 25, 2019, which claims the benefit of European Patent Application No. 18209956.4, filed on Dec. 4, 2018.

The invention relates to a process for the preparation of 5-bromo-1,3-dichloro-2-fluoro-benzene of formula I

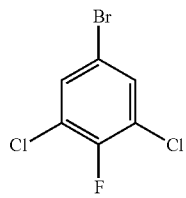

I by diazotization and reduction of 6-bromo-2,4-dichloro-3-fluoro-aniline of formula II,

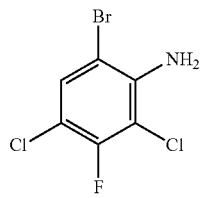

II 6-bromo-2,4-dichloro-3-fluoro-aniline of formula II is obtained by bromination of 2,4-dichloro-3-fluoro-aniline of formula III.

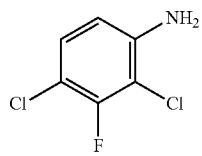

III 2,4-dichloro-3-fluoro-aniline of formula III is obtained by reduction of 1,3-dichloro-2-fluoro-4-nitro-benzene of formula IV.

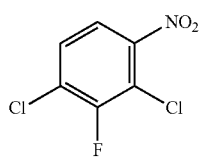

IV

Compound of formula I is a valuable intermediate for the preparation of active compounds of formula V

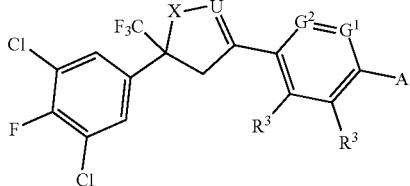

V wherein
X is CH, O, or S,
U is CH or N;
$G^1$, $G^2$ are each $CR^3$, or together form a sulfur atom; ze
each $R^3$ is independently H, halogen, CN, $N_3$, $NO_2$, SCN, $SF_5$, $C_1$-$C_6$-alkyl, $C_3$-$C_8$-cycloalkyl, $C_2$-$C_6$-alkenyl, $C_2$-$C_6$-alkynyl, which groups are unsubstituted, partially or fully halogenated and/or substituted with one or more same or different $R^8$,
$Si(R^{12})_3$, $OR^9$, $S(O)_nR^9$, $NR^{10a}R^{10b}$,
phenyl which is unsubstituted or partially or fully substituted with $R^{11}$, and a 3- to 10-membered saturated, partially or fully unsaturated heteromonocyclic or heterobicyclic ring containing 1, 2, 3 or 4 heteroatoms N, O, and/or S as ring members, which ring is unsubstituted, or substituted with one or more same or different $R^{11}$, preferably the unsubstituted or substituted HET;
n is 0, 1, or 2;
or two $R^3$ bonded to adjacent carbon atoms may form a five- or six membered saturated, partially or fully unsaturated carbocyclic ring, or a dihydrofuran, or
$R^3$ bonded to carbon atom in position $G^1$ form a bond to the chain *-Q-Z— in group $A^2$;
A is a group $A^1$, $A^2$, $A^3$, or $A^4$; wherein
  $A^1$ is C(=W)Y;
    W is O, or S;
    Y is $N(R^5)R^6$, or $OR^9$;
  $A^2$ is

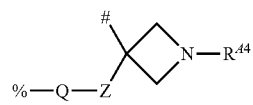

wherein #denotes the bond of group A, and % denotes the bond to $G^1$;
Q-Z is %—$CH_2$—O—*, %—$CH_2$—$S(O)_n$—*, or %—C(=O)—O—*, wherein % marks the bond of Q to phenyl, and *the bond of Z to azetidin; and
$R^{44}$ is H or C(=O)$R^{44}$, wherein
  $R^{44}$ is H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkylcarbonyl, which aliphatic groups are unsubstituted or substituted with one or more radicals $R^{41}$; $C_3$-$C_6$-cycloalkyl, $C_3$-$C_6$-halocycloalkyl which cyclic groups are unsubstituted or substituted with one or more $R^{42}$;
  C(=O)N($R^{43}$)$R^{44}$, N($R^{43}$)$R^{45}$, CH=NOR$^{46}$;
  phenyl, heterocycle, or hetaryl HET which rings are unsubstituted or partially or fully substituted with $R^4$;
$R^{41}$ is independently OH, CN, $C_1$-$C_6$-alkoxy, $C_1$-$C_6$-haloalkoxy, $S(O)_n$—$C_1$-$C_6$-alkyl, $S(O)_n$—$C_1$-$C_6$-haloalkyl, C(=O)N($R^{43}$)$R^{44}$, $C_3$-$C_6$-cycloalkyl, or $C_3$-$C_6$-halocycloalkyl which cycles are unsubstituted or substituted with one or more $R^{411}$; or phenyl, heterocycle or hetaryl HET which rings are unsubstituted or partially or fully substituted with $R^A$;

$R^{411}$ is independently OH, CN, $C_1$-$C_2$-alkyl, or $C_1$-$C_2$-haloalkyl;

$R^{43}$ is H, or $C_1$-$C_6$-alkyl, $R^{44}$ is H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, or $C_3$-$C_6$-cycloalkyl, $C_3$-$C_6$-halocycloalkyl, $C_3$-$C_6$-cycloalkylmethyl, or $C_3$-$C_6$-halocycloalkylmethyl which rings are unsubstituted or substituted with a cyano;

$R^{45}$ H, $C_1$-$C_6$-alkyl, $C_1$-$C_6$-haloalkyl, $C_2$-$C_4$-alkenyl, $C_2$-$C_4$-alkynyl, $CH_2$—CN, $C_3$-$C_6$-cycloalkyl, $C_3$-$C_6$-halocycloalkyl, $C_3$-$C_6$-cycloalkylmethyl, $C_3$-$C_6$-halocycloalkylmethyl, phenyl and hetaryl HET which aromatic rings are unsubstituted or partially or fully substituted with $R^A$;

$R^{42}$ $C_1$-$C_6$-alkyl, $C_1$-$C_6$-haloalkyl, or a group as defined for $R^{41}$;

$R^{46}$ is independently H, $C_1$-$C_6$-alkyl, or $C_1$-$C_6$-haloalkyl;

$R^A$ is independently selected from halogen, CN, $NO_2$, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $S(O)_n$—$C_1$-$C_4$-alkyl, $S(O)_n$—$C_1$-$C_4$-haloalkyl, $C_1$-$C_4$-alkylcarbonyl, $C_1$-$C_4$-haloalkylcarbonyl, $C(=O)N(R^{43})R^{44}$; or two $R^A$ present on the same carbon atom of a saturated or partially saturated ring may form together =O or =S; or two $R^A$ present on the same S or SO ring member of a heterocyclic ring may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;

$A^3$ is $CH_2$—$NR^5C(=W)R^6$;

$A^4$ is cyano;

$R^5$ is independently selected from the meanings mentioned for $R^2$;

$R^6$ is H, CN, $C_1$-$C_{10}$-alkyl, $C_3$-$C_8$-cycloalkyl, $C_2$-$C_{10}$-alkenyl, $C_2$-$C_{10}$-alkynyl, which groups are unsubstituted, partially or fully halogenated and/or substituted with one or more same or different $R^8$;

or $S(O)_nR^9$, or $C(=O)R^8$;

a 3- to 8-membered saturated, partially or fully unsaturated heterocyclic ring, which ring may contain 1, 2, 3, or 4 heteroatoms O, S, N, C=O and/or C=S as ring members, which heterocyclic ring is unsubstituted or partially or fully substituted with same or different halogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, which groups are unsubstituted, or partially or fully substituted with same or different $R^8$, or phenyl which may be partially or fully substituted with $R^{11}$;

or $R^5$ and $R^6$, together with the nitrogen atom to which they are bound, form a 3- to 8-membered saturated, partially or fully unsaturated heterocyclic ring, which ring may contain 1, 2, or 4 heteroatoms O, S, N, C=O and/or C=S as ring members, which heterocyclic ring is unsubstituted or partially or fully substituted with same or different halogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, which groups are unsubstituted, or partially or fully substituted with same or different $R^8$, or phenyl which may be partially or fully substituted with $R^{11}$;

or $R^5$ and $R^6$ together form a group =$C(R^8)_2$, =$S(O)_m(R^9)_2$, =$NR^{10a}$, or =$NOR^9$;

$R^{7a}$, $R^{7b}$ are each independently H, halogen, CN, $C_1$-$C_6$-alkyl, $C_3$-$C_8$-cycloalkyl, $C_2$-$C_6$-alkenyl, or $C_2$-$C_6$-alkynyl, which groups are unsubstituted, partially or fully halogenated and/or substituted with same or different $R^8$;

each $R^8$ is independently CN, $N_3$, $NO_2$, SCN, $SF_5$, $C_3$-$C_8$-cycloalkyl, $C_3$-$C_8$-halocycloalkyl, wherein the carbon chains may be substituted with one or more $R^{13}$;

$Si(R^{12})_3$, $OR^9$, $OSO_2R^9$, $S(O)_nR^9$, $N(R^{10a})R^{10b}$, $C(=O)N(R^{10a})R^{10b}$, $C(=S)N(R^{10a})R^{10b}$, $C(=O)OR^9$, $CH=NOR^9$, phenyl, which is unsubstituted or partially or fully substituted with same or different $R^{16}$, or a 3-, 4-, 5-, 6- or 7-membered saturated, partially or fully unsaturated heterocyclic ring comprising 1, 2 or 3 heteroatoms N, O, and/or S as ring members, which ring is unsubstituted or partially or fully substituted with same or different $R^{16}$, or two $R^8$ present on the same carbon atom of an alkyl, alkenyl, alkynyl or cycloalkyl group together form a group =O, =$C(R^{13})_2$; =S; =$S(O)_m(R^{15})_2$, =$S(O)_mR^{15}N(R^{14a})R^{14b}$, =$NR^{10a}$, =$NOR^9$; or =$NN(R^{10a})R^{10b}$; or two radicals $R^8$, together with the carbon atoms of the alkyl, alkenyl, alkynyl or cycloalkyl group which they are bonded to, form a 3-, 4-, 5-, 6-, 7- or 8-membered saturated or partially unsaturated carbocyclic or heterocyclic ring, which heterocyclic ring comprises 1, 2, 3 or 4 heteroatoms N, O, and/or S as ring members, and which ring is unsubstituted, or partially or fully substituted with same or different $R^{16}$; and $R^8$ as a substituent on a cycloalkyl ring may additionally be $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, and $C_2$-$C_6$-haloalkynyl, which groups are unsubstituted, or partially or fully substituted with same or different $R^{13}$; and $R^8$ in the groups $C(=O)R^8$ and =$C(R^8)_2$ may additionally be H, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, or $C_2$-$C_6$-haloalkynyl, which groups are unsubstituted, or partially or fully substituted with same or different $R^{13}$;

each $R^9$ is independently H, CN, $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl-, $C_3$-$C_8$-halocycloalkyl, $C_2$-$C_6$-alkenyl, $C_2$-$C_6$-haloalkenyl, $C_2$-$C_6$-alkynyl, or $C_2$-$C_6$-haloalkynyl, which groups are unsubstituted, or partially or fully substituted with same or different $R^{13}$, or $C_1$-$C_6$-alkyl-$C(=O)OR^{15}$, $C_1$-$C_6$-alkyl-$C(=O)N(R^{14a})R^{14b}$, $C_1$-$C_6$-alkyl-$C(=S)N(R^{14a})R^{14b}$, $C_1$-$C_6$-alkyl-$C(=NR^{14})N(R^{14a})R^{14b}$, $Si(R^{12})_3$, $S(O)_nR^{15}$, $S(O)_nN(R^{14a})R^{14b}$, $N(R^{10a})R^{10b}$, $N=C(R^{13})_2$, $C(=O)R^{13}$, $C(=O)N(R^{14a})R^{14b}$, $C(=S)N(R^{14a})R^{14b}$, $C(=O)OR^{15}$, or phenyl, which is unsubstituted, or partially or fully substituted with $R^{16}$; and a 3- to 7-membered saturated, partially or fully unsaturated heterocyclic ring comprising 1, 2 or 3 heteroatoms N, O, and/or S as ring members, which ring is unsubstituted, or partially or fully substituted with same or different $R^{16}$; and $R^9$ in the groups $S(O)_nR^9$ and $OSO_2R^9$ may additionally be $C_1$-$C_6$-alkoxy, or $C_1$-$C_6$-haloalkoxy;

$R^{10a}$, $R^{10b}$ are independently from one another H, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, which groups are unsubstituted, or partially or fully substituted with same or different $R^{13}$;

$C_1$-$C_6$-alkyl-C(=O)$OR^{15}$, $C_1$-$C_6$-alkyl-C(=O)N($R^{14a}$)$R^{14b}$, $C_1$-$C_6$-alkyl-C(=S)N($R^{14a}$)$R^{14b}$, $C_1$-$C_6$-alkyl-C(=$NR^{14}$)N($R^{14a}$)$R^{14b}$, $C_1$-$C_6$-alkoxy, $C_1$-$C_6$-haloalkoxy, $C_1$-$C_6$-alkylthio, $C_1$-$C_6$-haloalkylthio, $S(O)_nR^{15}$, $S(O)_nN(R^{14a})R^{14b}$, C(=O)$R^{13}$, C(=O)$OR^{15}$, C(=O)N($R^{14a}$)$R^{14b}$, C(=S)$R^{13}$, C(=S)$SR^{15}$, C(=S)N($R^{14a}$)$R^{14b}$, C(=$NR^{14}$)$R^{13}$;

phenyl, which is unsubstituted, or partially or fully substituted with same or different $R^{16}$; and a 3-, 4-, 5-, 6- or 7-membered saturated, partially or fully unsaturated heterocyclic ring comprising 1, 2, 3 or 4 heteroatoms N, O, and/or S as ring members, which ring is unsubstituted, or partially or fully substituted with same or different $R^{16}$, preferably unsubstituted or substituted HET; or $R^{10a}$ and $R^{10b}$ together with the nitrogen atom they are bonded to form a 3- to 8-membered saturated, partially or fully unsaturated heterocyclic ring, which ring may additionally contain one or two heteroatoms N, O, and/or S as ring members, which ring is unsubstituted, or partially or fully substituted with same or different halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be partially or fully substituted with $R^{16}$, and a 3-, 4-, 5-, 6-, or 7-membered saturated, partially or fully unsaturated heterocyclic ring comprising 1, 2 or 3 heteroatoms N, O, and/or S as ring members, which ring is unsubstituted, or partially or fully substituted with same or different $R^{16}$; or $R^{10a}$ and $R^{10b}$ together form a group =C($R^{13}$)$_2$, =S(O)$_m$($R^{15}$)$_2$, =S(O)$_mR^{15}$N($R^{14a}$)$R^{14b}$, =NR, or =$NOR^{15}$;

$R^{11}$ is halogen, CN, $N_3$, $NO_2$, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, which groups are unsubstituted, partially or fully halogenated, and/or may be substituted with same or different $R^8$, or $OR^9$, $NR^{10a}R^{10b}$, $S(O)_nR^9$, Si($R^{12}$)$_3$;

phenyl, which is unsubstituted, or partially or fully substituted with same or different $R^{16}$; and a 3- to 7-membered saturated, partially or fully unsaturated aromatic heterocyclic ring comprising 1, 2, 3, or 4 heteroatoms N, O, and/or S as ring members, which ring is unsubstituted, or partially or fully substituted with same or different $R^{16}$; or two $R^{11}$ present on the same ring carbon atom of an unsaturated or partially unsaturated heterocyclic ring may together form a group =O, =C($R^{13}$)$_2$, =S, =S(O)$_m$($R^{15}$)$_2$, =S(O)$_mR^{15}$N($R^{14a}$)$R^{14b}$, =$NR^{14}$, =$NOR^{15}$, or =NN($R^{14a}$)$R^{14b}$;

or two $R^{11}$ bound on adjacent ring atoms form together with the ring atoms to which they are bound a saturated 3- to 9-membered ring, which ring may contain 1 or 2 heteroatoms O, S, N, and/or $NR^{14}$, and/or 1 or 2 groups C=O, C=S, C=$NR^{14}$ as ring members, and which ring is unsubstituted, or partially or fully substituted with same or different halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be partially or fully substituted with same or different $R^{16}$, and a 3- to 7-membered saturated, partially or fully unsaturated heterocyclic ring containing 1, 2, or 3 heteroatoms N, O, and/or S as ring members, which ring is unsubstituted, or partially or fully substituted with same or different $R^{16}$;

each $R^{12}$ is independently $C_1$-$C_4$-alkyl and phenyl, which is unsubstituted, or partially or fully substituted with same or different $C_1$-$C_4$-alkyl;

each $R^{13}$ is independently CN, $NO_2$, OH, SH, SCN, $SF_5$, $C_1$-$C_6$-alkoxy, $C_1$-$C_6$-haloalkoxy, $SO_n$—$C_1$-$C_6$-alkyl, $SO_n$—$C_1$-$C_6$-haloalkyl, Si($R^{12}$)$_3$, —C(=O)N($R^{14a}$)$R^{14b}$, $C_3$-$C_8$-cycloalkyl which is unsubstituted, partially or fully halogenated or substituted with 1 or 2 same or different $C_1$-$C_4$-alkyl, $C_3$-$C_4$-cycloalkyl, $C_1$-$C_4$-alkoxy, $C_1$-$C_4$-haloalkoxy and/or oxo; phenyl, benzyl, phenoxy, where the phenyl moiety may be substituted with one or more same or different $R^{16}$; and a 3- to 7-membered saturated, partially or fully unsaturated heterocyclic ring containing 1, 2, or 3 heteroatoms N, O, and/or S, as ring members, which ring is unsubstituted, or partially or fully substituted with same or different $R^{16}$; or two $R^{13}$ present on the same carbon atom of an alkyl, alkenyl, alkynyl or cycloalkyl group may together be =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl); and $R^{13}$ as a substituent of a cycloalkyl ring may additionally be $C_1$-$C_6$-alkyl, $C_2$-$C_6$-alkenyl or $C_2$-$C_6$-alkynyl, which groups are unsubstituted, partially or fully halogenated, or substituted with 1 or 2 CN, $C_3$-$C_4$-cycloalkyl, $C_1$-$C_4$-alkoxy, $C_1$-$C_4$-haloalkoxy, and oxo; and $R^{13}$ in groups =C($R^{13}$)$_2$, N=C($R^{13}$)$_2$, C(=O)$R^{13}$, C(=S)$R^{13}$, and C(=$NR^{14}$)$R^{13}$ may additionally be H, halogen, $C_1$-$C_6$-alkyl, $C_2$-$C_6$-alkenyl, or $C_2$-$C_6$-alkynyl, which groups are unsubstituted, partially or fully halogenated, or substituted with 1 or 2 CN, $C_3$-$C_4$-cycloalkyl, $C_1$-$C_4$-alkoxy, $C_1$-$C_4$-haloalkoxy, and oxo;

each $R^{14}$ is independently H, CN, $C_1$-$C_6$-alkoxy, $C_1$-$C_6$-haloalkoxy, $SO_n$—$C_1$-$C_6$-alkyl, $SO_n$—$C_1$-$C_6$-haloalkyl, Si($R^{12}$)$_3$;

$C_1$-$C_6$-alkyl, $C_2$-$C_6$-alkenyl, $C_2$-$C_6$-alkynyl, which groups are unsubstituted, partially or fully halogenated, or substituted with 1 or 2 CN, $C_1$-$C_4$-alkoxy, $C_1$-$C_4$-haloalkoxy, $SO_n$—$C_1$-$C_4$-alkyl, $C_3$-$C_6$-cycloalkyl which is unsubstituted or substituted with 1 or 2 substituents halogen and CN;

and oxo;

$C_3$-$C_8$-cycloalkyl which is unsubstituted, or partially or fully halogenated or substituted with 1 or 2 CN, $C_1$-$C_4$-alkyl, $C_1$-$C_4$-alkoxy, $C_1$-$C_4$-haloalkoxy, $SO_n$—$C_1$-$C_6$-alkyl, $C_3$-$C_4$-cycloalkyl, $C_3$-$C_4$-cycloalkyl-$C_1$-$C_4$-alkyl-, which groups are unsubstituted, or substituted with 1 or 2 substituents selected from halogen and CN;

phenyl, benzyl, pyridyl, phenoxy, which cyclic moieties are unsubstituted, or substituted with one or more same or different halogen, CN, $NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, and $C_1$-$C_6$-alkoxycarbonyl; and a 3-, 4-, 5- or 6-membered saturated, partially or fully unsaturated heterocyclic ring comprising 1, 2 or 3 heteroatoms N, O, and/or S as ring members, which ring is unsubstituted, or partially or fully substituted with same or different $R^{16}$;

$R^{14a}$ and $R^{14b}$ independently of each other, have one of the meanings given for $R^{14}$; or $R^{14a}$ and $R^{14b}$, together with the nitrogen atom to which they are bound, form a 3- to 7-membered saturated, partially, or fully unsaturated heterocyclic ring, wherein the ring may additionally contain 1 or 2 heteroatoms N, O, and/or S as ring members, which ring is unsubstituted, or partially or fully substituted with same or different halogen, $C_1$-$C_4$-alkyl, $C_1$-$C_4$-haloalkyl, $C_1$-$C_4$-alkoxy, or $C_1$-$C_4$-haloalkoxy; or $R^{14a}$ and $R^{14}$ or $R^{14b}$ and $R^{14}$, together with the nitrogen atoms to which they are bound in the group $C(=NR^{14})N(R^{14a})R^{14b}$, form a 3- to 7-membered partially, or fully unsaturated heterocyclic ring, wherein the ring may additionally contain 1 or 2 heteroatoms N, O, and/or S as ring members, which ring is unsubstituted, or partially or fully substituted with same or different halogen, $C_1$-$C_4$-haloalkyl, $C_1$-$C_4$-alkoxy, or $C_1$-$C_4$-haloalkoxy;

each $R^{15}$ is independently H, CN, $Si(R^{12})_3$ $C_1$-$C_6$-alkyl, $C_2$-$C_6$-alkenyl, $C_2$-$C_6$-alkynyl, which groups are unsubstituted, partially or fully halogenated, or substituted with 1 or 2 radicals $C_3$-$C_4$-cycloalkyl, $C_1$-$C_4$-alkoxy, $C_1$-$C_4$-haloalkoxy, $SO_n$—$C_1$-$C_6$-alkyl, or oxo;

$C_3$-$C_8$-cycloalkyl which is unsubstituted, partially or fully halogenated or substituted with 1 or 2 radicals $C_1$-$C_4$-alkyl, $C_3$-$C_4$-cycloalkyl, $C_1$-$C_4$-alkoxy, $C_1$-$C_4$-haloalkoxy, $SO_n$—$C_1$-$C_6$-alkyl, or oxo;

phenyl, benzyl, pyridyl, and phenoxy, which rings are unsubstituted, partially or fully halogenated, or substituted with 1, 2 or 3 substituents $C_1$-$C_6$-alkyl, $C_1$-$C_6$-haloalkyl, $C_1$-$C_6$-alkoxy, $C_1$-$C_6$-haloalkoxy, or $(C_1$-$C_6$-alkoxy)carbonyl;

each $R^{16}$ is independently halogen, $NO_2$, CN, OH, SH, $C_1$-$C_6$-alkoxy, $C_1$-$C_6$-haloalkoxy, $SO_n$—$C_1$-$C_6$-alkyl, $SO_n$—$C_1$-$C_6$-haloalkyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, aminocarbonyl, $C_1$-$C_4$-alkylaminocarbonyl, di-($C_1$-$C_4$-alkyl)-aminocarbonyl, $Si(R^{12})_3$; $C_1$-$C_6$-alkyl, $C_2$-$C_6$-alkenyl, $C_2$-$C_6$-alkynyl, which groups are unsubstituted, partially or fully halogenated, or substituted with 1 or 2 radicals CN, $C_3$-$C_4$-cycloalkyl, $C_1$-$C_4$-alkoxy, $C_1$-$C_4$-haloalkoxy, or oxo;

$C_3$-$C_8$-cycloalkyl which is unsubstituted, partially or fully halogenated or substituted with 1 or 2 radicals CN, $C_1$-$C_4$-alkyl, $C_3$-$C_4$-cycloalkyl, $C_1$-$C_4$-alkoxy, $C_1$-$C_4$-haloalkoxy, or oxo;

phenyl, benzyl, pyridyl and phenoxy, which rings are unsubstituted, partially or fully halogenated, or substituted with 1, 2 or 3 substituents $C_1$-$C_6$-alkyl, $C_1$-$C_6$-haloalkyl, $C_1$-$C_6$-alkoxy, $C_1$-$C_6$-haloalkoxy, or $(C_1$-$C_6$-alkoxy)carbonyl; or two $R^{16}$ present together on the same atom of an unsaturated or partially unsaturated ring may be =O, =S, =N($C_1$-$C_6$-alkyl), =NO—$C_1$-$C_6$-alkyl, =CH($C_1$-$C_4$-alkyl), or =C($C_1$-$C_4$-alkyl)$_2$; or two $R^{16}$ on two adjacent carbon atoms form together with the carbon atoms they are bonded to a 4- to 8-membered saturated, partially or fully unsaturated ring, wherein the ring may contain 1 or 2 heteroatoms N, O, and/or S as ring members, which ring is unsubstituted, or partially or fully substituted with same or different halogen, $C_1$-$C_4$-alkyl, $C_1$-$C_4$-haloalkyl, $C_1$-$C_4$-alkoxy, or $C_1$-$C_4$-haloalkoxy;

each m is independently 0, or 1.

Compounds V are known from WO 2013/026929, WO 2012/163959, WO 2012/007426, WO 2011/067272, WO 2010/149506, WO 2010/020522, WO 2009/080250, WO 2016/102482, and EP-A-1731512 to have pesticidal activity.

CN 103664511 discloses a method for preparation of compound I by fluorine Sandmeyer reaction starting from 3,5-dichloro-4-fluoro-aniline VI. However, compound VI of the above process is formed by a nitration reaction of dichlorofluorobenzene in an unselective nitration reaction, which is low yielding and gives a mixture of nitro isomers. After separation and isolation of the desired isomer and reduction of the nitro group, aniline compound VI can be obtained.

WO 2016/058895 discloses deprotonation of 1-bromo-4-fluoro-benzene with a magnesium amide base and reaction with a halogenating agent to yield compound I. However, the employed base involves lithium salts which are expensive on large scale. The described catalysts include hexamethyl phosphoric acid triamide, which is highly carcinogenic. The selectivity of the chlorination as described in the provided protocol is up to 12:1 and requires purification measures by silica gel chromatography. Such purification is difficult to be performed on large scale. Hence this process is not applicable to manufacture in industrial scale.

The objective task of the invention is providing an economical, industrially applicable manufacturing process for synthesis of 5-bromo-1,3-dichloro-2-fluoro-benzene. Accordingly, the above defined process was found.

In the inventive process 5-bromo-1,3-dichloro-2-fluoro-benzene 6-bromo-2,4-dichloro-3-fluoro-aniline is diazotized under acidic conditions to the salt of formula IIa wherein X⁻ is a counteranion of the acid, preferably a chloride anion, which salt is then reduced to 5-bromo-1,3-dichloro-2-fluoro-benzene

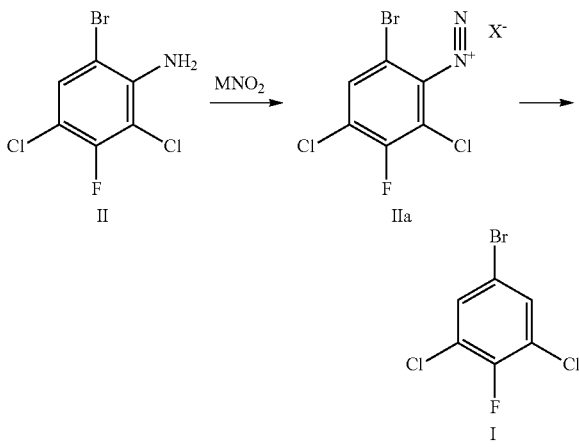

The diazotization is usually carried out at temperatures of from −20° C. to +20° C., preferably from −10° C. to +10° C., in an inert solvent, in the presence of alkali metal and alkaline earth metal nitrites or organic nitrites, such as methyl nitrite, ethyl nitrite, n-propyl nitrite, isopropyl nitrite, n-butylnitrite, sec-butyl nitrite, isobutyl nitrite, tert-butyl nitrite, isoamyl nitrite, tert-amylnitrite and an acid, preferably HCl [cf. Organic Syntheses, 31, 96-101; 1951].

Suitable solvents are water, alcohols such as methanol, ethanol, n-propanol, isopropanol, n-butanol, and tert.-butanol, moreover dimethyl sulphoxide (DMSO), dimethyl formamide (DMF), and dimethylacetamide (DMA), preferably water and methanol or ethanol, particularly preferred is water. It is also possible to use mixtures of the solvents mentioned.

Suitable acids and acidic catalysts are in general inorganic acids such as hydrofluoric acid (HF), hydrochloric acid (HCl), hydrobromic acid (HBr), sulphuric acid ($H_2SO_4$), ($HBF_4$) tetrafluoro boric acid and perchloric acid ($HClO_4$). The acids are generally employed in stoichiometric amounts; however, they can also be used in equimolar amounts, in excess or, if appropriate, as solvent.

The alkaline or earth alkaline metal nitrite is preferably $NaNO_2$, $KNO_2$, or $Ca(NO_2)_2$. The organic nitrites, is preferably methyl nitrite, ethyl nitrite, n-propyl nitrite, isopropyl nitrite, n-butylnitrite, sec-butyl nitrite, isobutyl nitrite, tert-butyl nitrite, isoamyl nitrite, tert-amylnitrite.

The starting materials are generally reacted with one another in equimolar amounts. In terms of yield, it may be advantageous to employ an excess of alkaline or earth alkaline metal nitrite or organic nitrites, based on II.

The reduction of IIa to yield I is usually carried out at temperatures of from +20° C. to +100° C., preferably from 50° C. to 95° C., in an inert solvent, in the presence of a reducing agent [cf. Tetrahedron Letters, 41(29), 5567-5569; 2000].

Suitable solvents are alcohols such as methanol, ethanol, n-propanol, isopropanol, n-butanol, and tert.-butanol, moreover DMSO, DMF, and DMA, and water; preferably DMF and water. It is also possible to use mixtures of the solvents mentioned.

Suitable reducing agents are compounds such as hypophosphorous acid or iron (II) sulfate.

The reducing agents are generally employed in stoichiometric amounts; however, they can also be used in excess or, if appropriate, as solvent.

The starting materials are generally reacted with one another in equimolar amounts. In terms of yield, it may be advantageous to employ an excess of the reducing agent based on IIa.

6-bromo-2,4-dichloro-3-fluoro-aniline of formula II is obtained by bromination of 2,4-dichloro-3-fluoro-aniline of formula III,

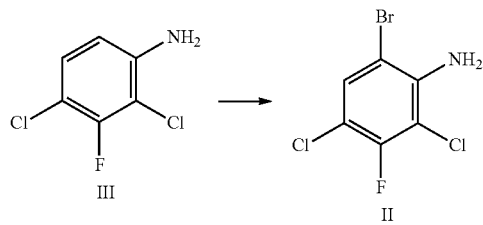

Suitable reaction conditions are described in literature (cf. US2010/196321). Suitable bromination agents are bromine, N-bromosuccinimide ("NBS"), dimethyl dibromo hydantoine (DBDMH), dibromoisocyanuric acid (DBI), phenyltrimethylammonium tribromide, copper(II)bromide. The bromination agent is preferably selected from bromine, DBDMH, and NBS. Optionally, an acid can be employed in the reaction such as a Brønsted acid like acetic acid, HBr, HCl, $H_2SO_4$, oleum with different $SO_3$-contents, toluene sulphonic acid (TsOH), methane sulfonic acid, or Lewis acids such as $AlCl_3 \cdot AlBr_3$, $AlCF_3$, Fe-powder, $FeCl_3$, and $FeBr_3$. Suitable solvents are halogenated hydrocarbons such as dichloromethane, chloroform, 1,2-dichloroethane, or ethers such as tetrahydrofurane (THF), diethylether, tert.-butylmethylether (TBME), 1,4-dioxane, or alcohols such as methanol, ethanol, and the like, or ethyl acetate, butyl acetate, acetic acid, moreover dimethyl sulphoxide (DMSO), dimethyl formamide (DMF), N-methylpyrolidone NMP, dimethylpyrolidinedione DMI and dimethylacetamide (DMA), acetonitrile (AN) or water, or mixtures thereof.

This transformation is usually carried out at temperatures of from 0° C. to +110° C., preferably from 10° C. to +50° C., in an inert solvent, in the presence of hydrogen peroxide [cf. CN 103224452].

Suitable solvents are water, aliphatic hydrocarbons such as pentane, hexane, cyclohexane, and petrol ether, aromatic hydrocarbons such as toluene, o-, m-, and p-xylene, halogenated hydrocarbons such as methylene chloride, chloroform, and chlorobenzene, ethers such as diethylether, diisopropylether, TBME, dioxane, anisole, and THF, nitriles such as acetonitrile, and propionitrile, alcohols such as methanol, ethanol, n-propanol, isopropanol, n-butanol, and tert.-butanol, moreover DMSO, DMF, acetic acid and DMA, preferably water and acetic acid. It is also possible to use mixtures of the solvents mentioned.

Suitable acids and acidic catalysts are in general organic acids such as formic acid, acetic acid, propionic acid, oxalic acid, TsOH, benzene sulphonic acid, camphor sulphonic acid, citric acid, and trifluoro acetic acid (TFA). The acids are generally employed in catalytic amounts; however, they can also be used in equimolar amounts, in excess or, if appropriate, as solvent.

The starting materials are generally reacted with one another in equimolar amounts.

2,4-dichloro-3-fluoro-aniline of formula III is obtained by reduction of 1,3-dichloro-2-fluoro-4-nitro-benzene of formula IV.

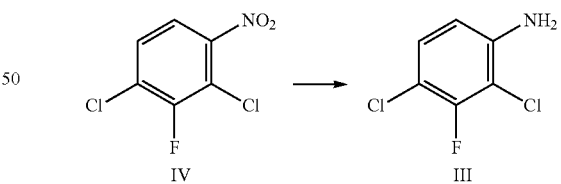

This transformation is usually carried out at temperatures of from 0° C. to +120° C., preferably from 10° C. to 70° C., more preferably 10° C. to 40° C., in an inert solvent in the presence of hydrogen and a catalyst [cf. Topics in Catalysis, 55(7-10), 505-511; 2012].

Suitable solvents are water, aliphatic hydrocarbons such as pentane, hexane, cyclohexane, cycloheptane and petrol ether, aromatic hydrocarbons such as toluene, o-, m-, and p-xylene, mesitylene, halogenated hydrocarbons such as methylene chloride, chloroform, and chlorobenzene, dichloro benzenes, benzotrifluoride, ethers such as diethylether, diisopropylether, tert.-butylmethylether, dioxane, anisole, and THF, methyltetrahydrofurane, cyclopentyl-methylether, esters such as methyl acetate, ethyl acetate, butyl acetate, ethyl propionate, ethylene carbonate, propylene carbonate, and the like, nitriles such as acetonitrile, and propionitrile, ketones such as acetone, methyl ethyl ketone, diethyl ketone, and tert.-butyl methyl ketone, methyl isopropyl ketone, acetophenone, alcohols such as methanol, ethanol, n-propanol, isopropanol, n-butanol, and tert.-butanol, moreover DMSO, sulfolane, DMF, diethyl formamide, NMP, DMI, DMPU and DMA, preferably water, methanol, ethanol, ethyl acetate, or toluene. It is also possible to use mixtures of the solvents mentioned.

Suitable bases are, in general, inorganic compounds, such as alkali metal and alkaline earth metal hydroxides, such as LiOH, NaOH, KOH and Ca(OH)$_2$, alkali metal and alkaline earth metal oxides, such as Li$_2$O, Na$_2$O, CaO, and MgO, alkali metal and alkaline earth metal hydrides, such as LiH, NaH, KH, and CaH$_2$, alkali metal and alkaline earth metal carbonates, such as Li$_2$CO$_3$, Na$_2$CO$_3$, K$_2$CO$_3$ and CaCO$_3$, and also alkali metal bicarbonates, such as NaHCO$_3$, moreover, organic bases, for example tertiary amines, such as trimethylamine, triethylamine, diisopropylethylamine and N-methylpiperidine, pyridine, substituted pyridines, such as collidines, lutidines, and 4-dimethylaminopyridine, and also bicyclic amines.

Examples of suitable reducing agents and conditions are known from the literature and can be found inter alia in *Advanced Organic Chemistry* (ed. J. March), 4$^{th}$ edition, Wiley-Interscience, N Y 1992, p. 1216 ff; or *Organikum*, 22$^{nd}$ edition, Wiley-VCH, Weinheim 2004, p. 626 ff.

Preferred examples are reducing agents like molecular hydrogen, hydrazine, borane, or borohydrides in combination with a homogeneous or heterogeneous catalysts from metal salts of nickel, palladium, platinum, cobalt, rhodium or iridium and copper. Specific examples include palladium on charcoal, palladium on alumina, platinum on charcoal, platinum(IV) oxide, Raney nickel, rhodium on alumina.

Suitable catalysts are platinum, palladium; nickel and molybdenum.

The bases are generally employed in catalytic amounts; however, they can also be used in equimolar amounts, in excess or, if appropriate, as solvent.

Suitable acids and acidic catalysts are in general inorganic acids such as HF, HCl, HBr, H$_2$SO$_4$ und HClO$_4$, Lewis acids, such as BF$_3$, AlCl$_3$, FeCl$_3$, SnCl$_4$, TiCl$_4$ and ZkCl$_2$, moreover organic acids such as formic acid, acetic acid, propionic acid, oxalic acid, TsOH, benzene sulphonic acid, camphor sulphonic acid, citric acid, and TFA.

The acids are generally employed in catalytic amounts; however, they can also be used in equimolar amounts, in excess or, if appropriate, as solvent.

The starting materials are generally reacted with one another in equimolar amounts. In terms of yield, it may be advantageous to employ an excess of II, based on III.

The starting material 1,3-dichloro-2-fluoro-4-nitro-benzene is commercially available or known from the literature [cf. Journal of the American Chemical Society (1959), 81, 94-101] or can be prepared in accordance with the literature cited. 6-bromo-2,4-dichloro-3-fluoro-aniline is known in the art (CAS 1360438-57-8).

The transformation from compound I to active compounds of formula V is known in the art.

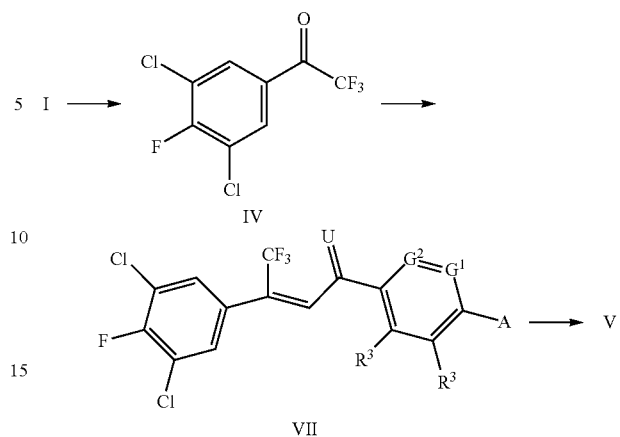

The reaction I→VI is usually carried out at temperatures of from −10° C. to 110° C., preferably from 0° C. to 60° C., in an inert solvent, in the presence of a Grignard reagent [cf. WO 2010125130]. The reaction VI→VII is usually carried out at temperatures of from 20° C. to 130° C., preferably from 50° C. to 110° C., in an inert solvent, in the presence of a base [cf. WO 2009126668].

Compounds VII are formed as mixtures of E- and Z-isomers, usually with predominant share of E-isomer. For clarity reasons formula VII is shown as Z-isomer only.

The reaction VII→V is usually carried out at temperatures of from −20° C. to +20° C., preferably from −10° C. to +5° C., in an inert solvent, in the presence of a base and a catalyst [cf. WO 2011067272].

The reaction mixtures are worked up in a customary manner, for example by mixing with water, separating the phases and, if appropriate, chromatographic purification of the crude products. Some of the intermediates and end products are obtained in the form of colourless or slightly brownish viscous oils which are purified or freed from volatile components under reduced pressure and at moderately elevated temperature. If the intermediates and end products are obtained as solids, purification can also be carried out by recrystallization or digestion.

The organic moieties mentioned in the above definitions of the variables are—like the term halogen—collective terms for individual listings of the individual group members. The prefix CO$_n$—C$_m$ indicates in each case the possible number of carbon atoms in the group.

The term halogen denotes in each case fluorine, bromine, chlorine, or iodine, in particular fluorine, chlorine, or bromine.

The term "alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("C$_1$-C$_2$-alkyl"), 1 to 3 ("C$_1$-C$_3$-alkyl"), 1 to 4 ("C$_1$-C$_4$-alkyl"), or 1 to 6 ("C$_1$-C$_6$-alkyl"). C$_1$-C$_4$-Alkyl is methyl (Me), ethyl (Et), propyl, isopropyl, butyl, 1-methylpropyl (sec-butyl), 2-methylpropyl (isobutyl) or 1,1-dimethylethyl (tert-butyl, $^t$Bu).

The term "haloalkyl" as used herein, which is also expressed as "alkyl which is partially or fully halogenated", refers to straight-chain or branched alkyl groups having 1 to 4 ("C$_1$-C$_4$-haloalkyl"), carbon atoms (as mentioned above), wherein some or all of the hydrogen atoms in these groups are replaced by halogen atoms as mentioned above: in particular C$_1$-C$_2$-haloalkyl.

"Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl"), carbon atoms and a double bond in any position.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl") carbon atoms and one or two triple bonds in any position, for example $C_2$-$C_4$-alkynyl, such as ethynyl, 1-propynyl, 2-propynyl, 1-butynyl, 2-butynyl, 3-butynyl, 1-methyl-2-propynyl and the like. The term "cycloalkyl" as used herein refers to mono- or bi- or polycyclic saturated hydrocarbon radicals having 3 to 8 ("$C_3$-$C_8$-cycloalkyl"), in particular 3 to 6 ("$C_3$-$C_6$-cycloalkyl") or 3 to 5 ("$C_3$-$C_5$-cycloalkyl") carbon atoms. Examples of monocyclic radicals having 3 to 6 carbon atoms comprise cyclopropyl (c-$C_3H_5$), cyclobutyl (c-$C_4H_7$), cyclopentyl (c-$C_5H_9$) and cyclohexyl (c-$C_6H_{11}$). Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl. Preferably, the term cycloalkyl denotes a monocyclic saturated hydrocarbon radical.

The term "cycloalkyl-$C_1$-$C_4$-alkyl" refers to a $C_3$-$C_8$-cycloalkyl group ("$C_3$-$C_8$-cycloalkyl-$C_1$-$C_4$-alkyl"), preferably a $C_3$-$C_6$-cycloalkyl group ("$C_3$-$C_6$-cycloalkyl-$C_1$-$C_4$-alkyl"), more preferably a $C_3$-$C_4$-cycloalkyl group ("$C_3$-$C_4$-cycloalkyl-$C_1$-$C_4$-alkyl") as defined above (preferably a monocyclic cycloalkyl group) which is bound to the remainder of the molecule via a $C_1$-$C_4$-alkyl group, as defined above.

The term "$C_1$-$C_2$-alkoxy" is a $C_1$-$C_2$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom.

The term "$C_1$-$C_4$-alkoxy-methyl" as used herein, refers to methyl in which one hydrogen atom is replaced by a $C_1$-$C_4$-alkoxy group, as defined above. The term "$C_1$-$C_6$-alkoxy-methyl" as used herein, refers to methyl in which one hydrogen atom is replaced by a $C_1$-$C_6$-alkoxy group, as defined above.

The term "$SO_n$—$C_1$-$C_6$-alkyl" is a $C_1$-$C_6$-alkyl group, as defined above, attached via a sulfur atom, in case n is 0 (also referred to as alkylthio group). If n is 1, the term refers to a $C_1$-$C_6$-alkyl group attached via a sulfinyl group (also referred to as alkylsulfinyl group). If n is 2, the term refers to a $C_1$-$C_6$-alkyl group attached via a sulfonyl group (also referred to as alkylsulfonyl group).

The substituent "oxo" replaces a $CH_2$ group by a $C(\!=\!O)$ group.

The term "alkylcarbonyl" is a $C_1$-$C_6$-alkyl ("$C_1$-$C_6$-alkylcarbonyl"), preferably a $C_1$-$C_4$-alkyl ("$C_1$-$C_4$-alkylcarbonyl") group, as defined above, attached via a carbonyl [C(=O)] group. Examples are acetyl (methylcarbonyl), propionyl (ethylcarbonyl), propylcarbonyl, isopropylcarbonyl, n-butylcarbonyl and the like. The term "haloalkylcarbonyl" is a $C_1$-$C_6$-haloalkyl ("$C_1$-$C_6$-haloalkylcarbonyl"), preferably a $C_1$-$C_4$-haloalkyl ("$C_1$-$C_4$-haloalkylcarbonyl") group, as defined above, attached via a carbonyl [C(=O)] group.

The term "alkoxycarbonyl" is a $C_1$-$C_6$-alkoxy ("$C_1$-$C_6$-alkoxycarbonyl"), preferably a $C_1$-$C_4$-alkoxy ("$C_1$-$C_4$-alkoxycarbonyl") group, as defined above, attached via a carbonyl [C(=O)] group. The term "$C_1$-$C_4$-alkylamino" is a group —N(H)$C_1$-$C_4$-alkyl.

The term "$C_1$-$C_4$-alkylaminocarbonyl" is a group —C(O)N(H)$C_1$-$C_4$-alkyl.

The term "3-, 4-, 5-, 6-, 7-, 8-, 9- or 10-membered saturated, partially or fully unsaturated heterocyclic ring containing 1, 2 or 3 (or 4) heteroatoms N, O, and/or S, as ring members" denotes a 3-, 4-, 5-, 6-, 7- or 8-membered saturated, partially unsaturated or fully unsaturated heteromonocyclic ring or a 8-, 9- or 10-membered saturated, partially or fully unsaturated heterobicyclic ring containing 1, 2 or 3 (or 4) heteroatoms which are selected from N, O, and S as ring members. Unsaturated rings contain at least one C—C and/or C—N and/or N—N double bond(s). Fully unsaturated rings contain as many conjugated C—C and/or C—N and/or N—N double bonds as allowed by the ring size. Fully unsaturated include aromatic heterocyclic rings. The heterocyclic ring may be attached to the remainder of the molecule via a carbon ring member or via a nitrogen ring member. Of course, the heterocyclic ring contains at least one carbon ring atom. If the ring contains more than one O ring atom, these are not adjacent. N and S ring atoms may be oxidized, if not mentioned otherwise. The oxidized ring atoms constitute an N-oxide, Sulfoxide (SO), and a sulfone ($SO_2$), resp., wherein the only the N— or S atom is a ring member.

A group of preferred heterocycles is the following: 2-pyridyl (E-1), 3-pyridyl (E-2), 4-pyridyl (E-3), 3-pyridazinyl (E-4), 4-pyrimidinyl (E-5), 2-pyrazinyl (E-6), 2-pyrimidinyl (E-7), thiophen-2-yl (E-8), thiophen-3-yl (E-9), furan-2-yl (E-10), and furan-3-yl (E-11); heterocycles E-1, E-2, and E-7 are particularly preferred, which rings E-1 to E-11 are unsubstituted or substituted by up to 3 same or different substituents.

Another particularly preferred heterocycle is 1,2,4-triazol-1-yl.

Preferred 3-, 4-, 5-, 6- or 7-membered saturated, partially or fully unsaturated heterocyclic rings comprising 1, 2 or 3 heteroatoms N, O, and/or S as ring members (HET) are in any positions of formula I, the following: azetidin-3-yl (H-1), dioxin-6-yl (H-2), 1,3-dioxolan-2-yl (H-3), 1,1-dioxotetrahydrothiophene-3-yl (H-4), 1,1-dioxothietan-2-yl (H-5), 1,1-dioxothietan-3-yl (H-6), imidazol-2-yl (H-7), imidazol-4-yl (H-8), imidazol-5-yl (H-9), isothiazol-3-yl (H-10), isothiazol-4-yl (H-11), isothiazol-5-yl (H-12), isoxazol-3-yl (H-13), isoxazol-4-yl (H-14), isoxazol-5-yl (H-15), isoxazolidin-4-yl (H-16), oxazol-2-yl (H-17), oxazol-4-yl (H-18), oxazol-5-yl (H-19), oxethan-3-yl (H-20), 3-oxoisoxazolidin-4-yl (H-21), 2-oxopyrrolidin-3-yl (H-22), 2-oxotetrahydrofuran-3-yl (H-23), [1,3,4]-thiadiazol-2-yl (H-24), [1,2,3]-thiadiazol-4-yl (H-25), [1,2,3]-thiadiazol-5-yl (H-26), thiazol-2-yl (H-27), thiazol-4-yl (H-28), thiazol-5-yl (H-29), thien-2-yl (H-30), thien-3-yl (H-31), thietan-2-yl (H-32), thietan-3-yl (H-33), 1-oxothietan-2-yl (H-34), 1-oxothietan-3-yl (H-35), 1-oxotetrahydrothiophen-3-yl (H-36), tetrahydrofuran-2-yl (H-37), tetrahydrofuran-3-yl (H-38), tetrahydrothiophen-3-yl (H-39), pyrazin-2-yl (E-6), pyrazol-3-yl (H-40), 2-pyridyl (E-1), 3-pyridyl (E-2), 4-pyridyl (E-3), pyridazin-3-yl (E-4), pyridazin-4-yl (H-41), 2-pyrimidinyl (E-7), 4-pyrimidinyl (E-5), 5-pyrimidinyl (H-42), and pyrrolidin-3-yl (H-43). More preferred rings HET are the following: E-1, E-7 and H-6, H-21, H-33 and H-35. Rings E-2 and E-7 are particularly preferred.

In a particular embodiment, the variables of the compounds of the formula V have the following meanings, these meanings, both on their own and in combination with one another, being particular embodiments of the process of the invention.

The process is particularly suitable for compounds V wherein A is selected from $A^1$, $A^2$, and $A^3$.

In the compounds of the inventive process $R^1$ is preferably fluoromethyl, in particular $CF_3$.

$R^3$ is preferably H, halogen, or $CH_3$.

In a preferred embodiment $G^1$ and $G^2$ represent each $CR^3$, particularly $G^1$ is CH and $G^2$ is C—Cl, or C—$CH_3$.

In another embodiment $G^1$ and $G^2$ represent each $CR^3$, wherein the two $R^3$ form a five- or six membered saturated carbocyclic ring, or a dihydrofurane.

In another embodiment $G^1$ and $G^2$ together form a sulfur atom.

A preferred embodiment relates to the process for obtaining compounds I wherein A is $A^1$.

The processes for obtaining compounds V wherein A is $A^1$ start preferably from compounds of formula II wherein A is C(=O)Y, and Y is $OR^9$, preferably OH, or $C_1$-$C_4$-alkoxy, or $NR^5R^6$, wherein $R^5$ and $R^6$ are H or $C_1$-$C_4$-alkyl, preferably Y is $NHCH_3$. Particularly preferred A group in compounds I and its intermediates is an $C_1$-$C_4$-alkylester, such as C(=O)$OCH_3$.

In $A^1$ the variables $R^5$ and $R^6$ have preferably following meanings:

$R^5$ is preferably H, $C_1$-$C_4$-alkyl;

$R^6$ is preferably H, $C_1$-$C_6$-alkyl, $C_2$-$C_6$-alkenyl, which groups are substituted with one or more same or different $R^8$, wherein $R^8$ is preferably $C_3$-$C_8$-cycloalkyl, $C_3$-$C_8$-halocycloalkyl, wherein the carbon chains may be substituted with one or more $R^{13}$;

$S(O)_nR^9$, $N(R^{10a})R^{10b}$, C(=O)N($R^{10a}$)$R^{10b}$, C(=S)N($R^{10a}$)$R^{10b}$, C(=O)$OR^9$, CH=$NOR^9$, phenyl, which is unsubstituted or partially or fully substituted with same or different $R^{16}$, or a 3-, 4-, 5-, 6- or 7-membered saturated, partially or fully unsaturated heterocyclic ring comprising 1, 2 or 3 heteroatoms N, O, and/or S as ring members, which ring is unsubstituted or partially or fully substituted with same or different $R^{16}$, or a 5-membered saturated heteromonocyclic ring containing 1, or 2 heteroatoms N, O, and/or S as ring members, which ring is unsubstituted, or substituted with one or more same or different $R^{11}$, preferably the unsubstituted or substituted HET;

two $R^8$ present on the same carbon atom of an alkyl, alkenyl, alkynyl or cycloalkyl group together form a group =O, =C($R^{13}$)$_2$; =S; =S(O)$_m$($R^{15}$)$_2$, =S(O)$_m$$R^{15}$N($R^{14a}$)$R^{14b}$, =$NR^{10a}$, =$NOR^9$; or =NN($R^{10a}$)$R^{10b}$;

$R^9$ is preferably H, CN, $C_1$-$C_6$-alkyl, $C_1$-$C_6$-haloalkyl;

$R^{11}$ $C_1$-$C_{10}$-alkyl, which is unsubstituted, partially or fully halogenated, and/or may be substituted with same or different $R^8$, or $OR^9$, $NR^{10a}R^{10b}$, $S(O)_nR^9$;

two $R^{11}$ present on the same ring carbon atom of an unsaturated or partially unsaturated heterocyclic ring may together form a group =O, =C($R^{13}$)$_2$, =S, =S(O)$_m$($R^{15}$)$_2$, =S(O)$_m$$R^{15}$N($R^{14a}$)$R^{14b}$, =$NR^{14}$, =$NOR^{15}$, or =NN($R^{14a}$)$R^{14b}$.

Another embodiment relates to the process for obtaining compounds V wherein A is $A^2$, preferably wherein Q-Z is %—$CH_2$—O—*, and $R^4$ is $C_1$-$C_4$-alkylcarbonyl wherein the terminal C-atom of the alkyl is substituted with $S(O)_n$—$C_1$-$C_4$-alkyl.

Another embodiment relates to the process for obtaining compounds V wherein A is $A^3$, preferably $CH_2$—$NR^5C$(=O)$R^6$, wherein $R^5$ is H or $CH_3$, and $R^6$ is H, $C_1$-$C_6$-alkyl, $C_2$-$C_6$-alkenyl, which groups are substituted with one or more same or different $R^8$, wherein $R^8$ is as defined and preferred above.

Compounds V and its sub formulae wherein A is $A^4$ are intermediates in the inventive process.

The process is particularly suitable for synthesis of following active compounds of formula V, which correspond to formulae V.A, and V.B, wherein the variables are as defined and preferred above:

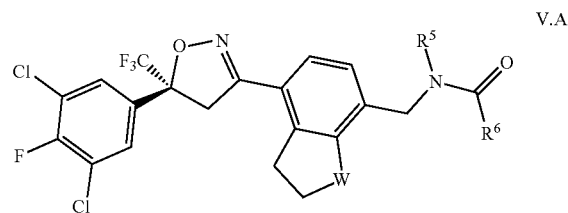

wherein W is CH or O; and

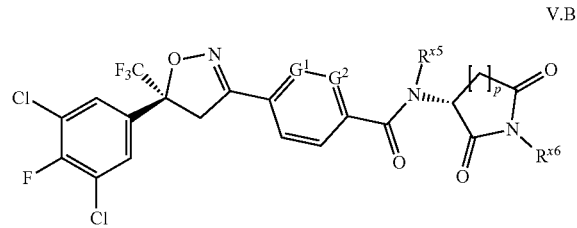

wherein p is 1 or 2; $R^{x5}$ is H or $CH_3$, and $R^{x6}$ is $C_1$-$C_6$-alkyl, $C_1$-$C_4$-haloalkyl, $C_3$-$C_6$-alkenyl, $C_3$-$C_6$-alkynyl, which groups may be substituted with C(=O)$OR^{a1}$, C(=O)N($R^{a2}$)$R^{a3}$, CH=$NOR^{a1}$, and phenyl, benzyl, which rings are unsubstituted or substituted with halogen, $C_1$-$C_4$-alkyl, or $C_1$-$C_4$-haloalkyl; wherein $R^{a1}$ is $C_1$-$C_6$-alkyl, $R^{a2}$ and $R^{a3}$ are each H or $C_1$-$C_6$-alkyl, $C_1$-$C_6$-haloalkyl, $C_2$-$C_4$-alkenyl, $C_2$-$C_4$-alkynyl.

Preferably $R^{x6}$ is $CH_3$, $C_2H_5$, $CH_2(CH_3)_2$, $CH_2CH=CH_2$, $CH_2CF_3$, $CH_2CH_2CF_3$, $CH_2C_6H_5$, or $CH_2C$(=O)$OCH_3$.

Preferably $G^1$, and $G^2$ are each $CR^3$; wherein each $R^3$ is H, halogen, or $C_1$-$C_6$-alkyl, particularly $G^1$, is CH, and $G^2$ is $CR^3$; wherein $R^3$ is halogen, or $C_1$-$C_2$-alkyl.

The process is furthermore particularly suitable for synthesis of following active compounds V.1, and V.2 of formula V which are known in the art (cf.: WO 2011/067272; WO 2012/120399):

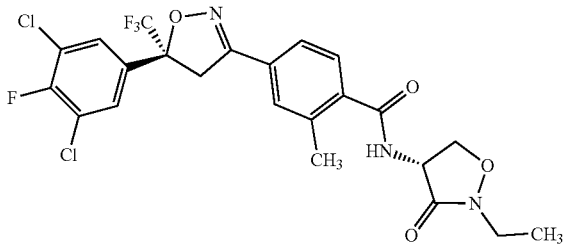

Isocycloseram

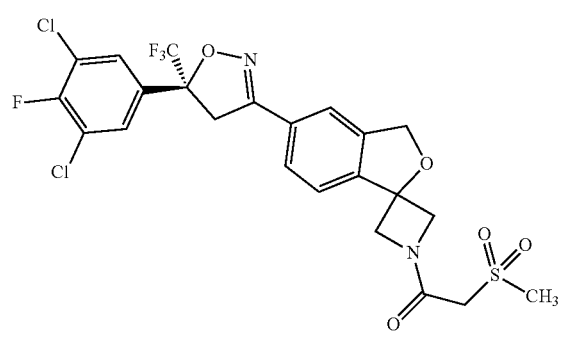

Sarolaner

Accordingly, the process is furthermore particularly suitable for synthesis of compounds of formula V, wherein
$R^1$ is $CF_3$;
$R^{2a}$ is F, Cl, Br, $CF_3$, or $OCF_3$;
$R^{2b}$ and $R^{2c}$ are independently from each other H, F, Cl, Br, $CF_3$, or $OCF_3$;
A is $A^1$, $A^2$, or $A^3$; wherein
  $A^1$ is $C(=O)N(R^5)R^6$, $C(=O)OR^9$, wherein
  $A^2$ is

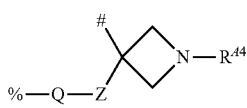

wherein #denotes the bond of group A, and % denotes the bond to $G^1$;
Q-Z is %—$CH_2$—O—*, wherein % marks the bond of Q to phenyl, and *the bond of Z to azetidin; and
$R^{44}$ is H, or $C(=O)R^{44}$, wherein
$R^{4A}$ is H, $C_1$-$C_4$-alkylcarbonyl, which is unsubstituted or substituted with $S(O)_n$—$C_1$-$C_6$-alkyl;
$A^3$ is $CH_2$—$NR^5C(=O)R^6$;
$G^1$, and $G^2$ are each $CR^3$, or together form a sulfur atom;
  $R^3$ is H or $C_1$-$C_4$-alkyl, or two $R^3$ bonded to adjacent carbon atoms may form a five- or six membered saturated or aromatic carbocyclic ring, or a dihydrofurane, or
  $R^3$ bonded to a carbon atom in position $G^1$ form a bond to the chain *-Q-Z— in group $A^2$;
$R^5$ is H;
$R^6$ is H, or $C_1$-$C_6$-alkyl which is unsubstituted, or substituted with one or two $R^8$;
or $R^5$ and $R^6$, together with the nitrogen atom to which they are bound, form a 5- or 6-membered saturated, heterocyclic ring, which ring contain 1 or 2 groups selected from O, S, N, and C=O as ring members, which heterocyclic ring is unsubstituted or partially substituted with same or different $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl;
each $R^8$ is $C(=O)N(R^{10a})R^{10b}$, or
two $R^8$ present on the same carbon atom of an alkyl group together form =$NOR^9$;
$R^9$ being $C_1$-$C_4$-alkyl;
$R^{10a}$, $R^{10b}$ are independently from one another H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl.
Such compounds represent formula Va.
The following examples illustrate the invention.

EXAMPLES

A. Preparation Examples

With appropriate modification of the starting materials, the procedures given in the synthesis description were used to obtain further compounds I. The compounds obtained in this manner are listed in the table that follows, together with physical data.

The products shown below were characterized by melting point determination, by NMR spectroscopy or by the masses ([m/z]) or retention time (RT; [min.]) determined by HPLC-MS or HPLC spectrometry.

HPLC-MS=high performance liquid chromatography-coupled mass spectrometry;

HPLC method A: HPLC Phenomenex Kinetex 1.7 μm XB-C18 100 A, 50×2.1 mm", Mobile Phase: A: water+0.1% TFA; B:CAN; Temperature: 60° C.; Gradient:5% B to 100% B in 1.50 min; 100% B 0.25 min; Flow: 0.8 ml/min to 1.0 ml/min in 1.51 min; MS method: ESI positive; Mass range (m/z): 100-700".

HPLC method B: HPLC method: Phenomenex Kinetex 1.7 μm XB-C18 100 A; 50×2.1 mm; mobile phase: A: water+0.1% trifluoroacetic acid (TFA); B: acetonitrile; gradient: 5-100% B in 1.50 minutes; 100% B 0.25 min; flow: 0.8-1.0 ml/min in 1.51 minutes at 60° C. MS: ESI positive, m/z 100-1400.

Example 1: Preparation of 2,4-dichloro-3-fluoro-aniline

A mixture of 1,3-dichloro-2-fluoro-4-nitro-benzene (24.9 g, 0.119 mol, 1.00 equiv.), Pt/C 5%/V 2.5% (2.00 g) and methanol (250 mL) was charged into a hydrogenation apparatus and flushed with hydrogen gas. A constant pressure of 0.1 bar hydrogen was kept throughout the reaction and the mixture was stirred at 2000 rpm keeping the temperature between 24-27° C. by cooling. After 0.5 h, the reaction was completed, and the catalyst was filtered off using a plug of celite. The filtrate was concentrated in vacuum to yield the title compound (21.1 g, purity 93%, yield 92%).

$^1$H NMR: (400 MHz, $CDCl_3$): δ 4.09 (br. s, 2H), 6.60 (m, 1H), 7.06 (m, 1H) ppm.

Example 2: Preparation of 6-bromo-2,4-dichloro-3-fluoro-aniline

To a mixture of 2,4-dichloro-3-fluoro-aniline (20.9 g, 0.110 mmol, 1.00 equiv.) and glacial acetic acid (92.7 g, 1.54 mol, 14 equiv.) was added bromine (10.58 g, 0.066 mol, 0.600 equiv.) at 20-22° C. within 25 min. After 5 min, hydrogen peroxide solution (50% in water, 4.502 g, 0.066 mol, 0.600 equiv.) was added and the temperature was maintained between 20-22° C. After 15 min, the reaction was completed and poured onto ice-water (300 mL). Excess of bromine was quenched by the addition of aqueous sodium sulfite solution. The resulting solids were collected by filtration and washed with water. Drying in vacuum at 40° C. yielded the title compound (29.60 g, purity 95%, yield 99%)

$^1$H NMR: (400 MHz, CDCl$_3$): δ 4.61 (br. s, 2H), 7.40 (m, 1H) ppm.

Example 3: Preparation of 5-bromo-1,3-dichloro-2-fluoro-benzene

A mixture of 6-bromo-2,4-dichloro-3-fluoro-aniline (29.5 g, 0.108 mmol, 1.00 equiv.) and concentrated hydrochloric acid (32% in water, 117 mL. 1.19 mol, 11 equiv.) was kept at 50° C. for 10 min and water was added. The resulting suspension was cooled to 0° C. and an aqueous solution of sodium nitrite (40.62 g, 25%, 0.147 mol, 1.40 equiv.) was added within 30 min, keeping the temperature between 0-2° C. for 1 h.

In a second flask, an aqueous solution of hypophosphoric acid (528 g, 50%, 4.01 mol, 37 equiv.) was heated to 90° C. and the diazonium solution from above was added within 10 min. After another 20 min at 85-90° C., the reaction was complete. The mixture was cooled and extracted with methylene chloride, combined organic layers were washed with water and dried over anhydrous magnesium sulfate. After filtration, the mother liquid was concentrated in vacuum to yield the title compound (23.5 g, purity 93%, yield 83%).

$^1$H NMR: (400 MHz, CDCl$_3$): δ 7.46 (m, 1H) ppm.

The invention claimed is:

1. A process for preparing 5-bromo-1,3-dichloro-2-fluoro-benzene comprising diazotizing 6-bromo-2,4-dichloro-3-fluoro-aniline and reducing the resulting diazonium salt to yield 5-bromo-1,3-dichloro-2-fluoro-benzene.

2. The process of claim 1, wherein 6-bromo-2,4-dichloro-3-fluoro-aniline is obtained by brominating 2,4-dichloro-3-fluoro-aniline.

3. The process of claim 2, wherein 2,4-dichloro-3-fluoro-aniline is obtained by reducing 1,3-dichloro-2-fluoro-4-nitro-benzene.

4. The process of claim 3, wherein the reduction is conducted with hydrogen on Pd/C catalyst.

5. The process of claim 2, wherein the bromination is conducted with bromine and an oxidation agent.

6. The process of claim 5, wherein the oxidation agent is $H_2O_2$.

7. The process of claim 1, wherein the diazotization is conducted with NaNO$_2$.

8. The process of claim 1, wherein the reduction of the diazonium salt is effected with hypophosphoric acid.

9. 6-bromo-2,4-dichloro-3-fluoro-aniline.

10. A process for preparing a compound of formula V

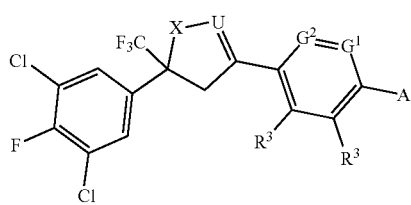

V wherein

X is CH, O, or S,

U is CH or N; each $R^2$ is independently H, halogen, CN, $N_3$, $NO_2$, SCN, $SF_5$, $C_1$-$C_6$-alkyl, $C_3$-$C_8$-cycloalkyl, $C_2$-$C_6$-alkenyl, $C_2$-$C_6$-alkynyl, which groups are unsubstituted, partially or fully halogenated and/or substituted with one or more same or different $R^8$, $Si(R^{12})_3$, $OR^9$, $S(O)_nR^9$, $NR^{10a}R^{10b}$, phenyl which is unsubstituted or partially or fully substituted with $R^{11}$, and a 3- to 10-membered saturated, partially or fully unsaturated heteromonocyclic or heterobicyclic ring containing 1, 2, 3 or 4 heteroatoms N, O, and/or S as ring members, which ring is unsubstituted, or substituted with one or more same or different $R^{11}$;

n is 0, 1, or 2;

$G^1$, $G^2$ are each $CR^3$, or together form a sulfur atom;

each $R^3$ is independently selected from the meanings mentioned for $R^2$, or two $R^3$ bonded to adjacent carbon atoms may form a five- or six membered saturated, partially or fully unsaturated carbocyclic ring, or a dihydrofurane, or $R^3$ bonded to carbon atom in position $G^1$ form a bond to the chain *-Q-Z— in group $A^2$;

A is a group $A^1$, $A^2$, $A^3$, or $A^4$; wherein
$A^1$ is C(=W)Y;
W is O, or S;
Y is $N(R^5)R^6$, or $OR^9$;
$A^2$ is

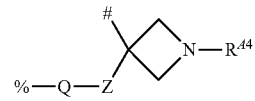

wherein #denotes the bond of group A, and % denotes the bond to $G^1$;

Q-Z is %—CH$_2$—O—*, %—CH$_2$—S(O)$_n$—*, or %—C(=O)—O—*, wherein % marks the bond of Q to phenyl, and *the bond of Z to azetidin; and $R^{44}$ is H or C(=O)$R^{44}$, wherein $R^{44}$ is H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkylcarbonyl, which aliphatic groups are unsubstituted or substituted with one or more radicals $R^{41}$;

$C_3$-$C_6$-cycloalkyl, $C_3$-$C_6$-halocycloalkyl which cyclic groups are unsubstituted or substituted with one or more $R^{42}$;

C(=O)N(R$^{43}$)R$^{44}$, N(R$^{43}$)R$^{45}$, CH=NOR$^{46}$;

phenyl, heterocycle, or hetaryl HET which rings are unsubstituted or partially or fully substituted with $R^4$;

$R^{41}$ is independently OH, CN, $C_1$-$C_6$-alkoxy, $C_1$-$C_6$-haloalkoxy, S(O)$_n$C$_1$-C$_6$-alkyl, S(O)$_n$C$_1$-C$_6$-haloalkyl, C(=O)N(R$^{43}$)R$^{44}$, $C_3$-$C_6$-cycloalkyl, or $C_3$-$C_6$-halocycloalkyl which cycles are unsubstituted or substituted with one or more $R^{411}$; or phenyl, heterocycle or hetaryl HET which rings are unsubstituted or partially or fully substituted with $R^4$;

$R^{411}$ is independently OH, CN, $C_1$-$C_2$-alkyl, or $C_1$-$C_2$-haloalkyl;

$R^{43}$ is H, or $C_1$-$C_6$-alkyl, $R^{44}$ is H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, or $C_3$-$C_6$-cycloalkyl, $C_3$-$C_6$-halocycloalkyl, $C_3$-$C_6$-cycloalkylmethyl, or $C_3$-$C_6$-halocycloalkylmethyl which rings are unsubstituted or substituted with a cyano;

$R^{45}$ H, $C_1$-$C_6$-alkyl, $C_1$-$C_6$-haloalkyl, $C_2$-$C_4$-alkenyl, $C_2$-$C_4$-alkynyl, $CH_2$—CN, $C_3$-$C_6$-cycloalkyl, $C_3$-$C_6$-halocycloalkyl, $C_3$-$C_6$-cycloalkylmethyl, $C_3$-$C_6$-halocycloalkylmethyl, phenyl and hetaryl HET which aromatic rings are unsubstituted or partially or fully substituted with $R^A$;

$R^{42}$ $C_1$-$C_6$-alkyl, $C_1$-$C_6$-haloalkyl, or a group as defined for $R^{41}$;

$R^{46}$ is independently H, $C_1$-$C_6$-alkyl, or $C_1$-$C_6$-haloalkyl;

$R^A$ is independently selected from halogen, CN, $NO_2$, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $S(O)_n$—$C_1$-$C_4$-alkyl, $S(O)_n$—$C_1$-$C_4$-haloalkyl, $C_1$-$C_4$-alkylcarbonyl, $C_1$-$C_4$-haloalkylcarbonyl, $C(=O)N(R^{43})R^{44}$; or two $R^A$ present on the same carbon atom of a saturated or partially saturated ring may form together =O or =S; or two $R^A$ present on the same S or SO ring member of a heterocyclic ring may together form a group =$N(C_1$-$C_6$-alkyl), =$NO(C_1$-$C_6$-alkyl), =$NN(H)(C_1$-$C_6$-alkyl) or =$NN(C_1$-$C_6$-alkyl)_2$;

$A^3$ is $CH_2$—$NR^5C(=W)R^6$;

$A^4$ is cyano;

$R^5$ is independently selected from the meanings mentioned for $R^2$;

$R^6$ is H, CN, $C_1$-$C_{10}$-alkyl, $C_3$-$C_8$-cycloalkyl, $C_2$-$C_{10}$-alkenyl, $C_2$-$C_{10}$-alkynyl, which groups are unsubstituted, partially or fully halogenated and/or substituted with one or more same or different $R^8$;

or $S(O)_nR^9$, or $C(=O)R^8$;

a 3- to 8-membered saturated, partially or fully unsaturated heterocyclic ring, which ring may contain 1, 2, 3, or 4 heteroatoms O, S, N, C=O and/or C=S as ring members, which heterocyclic ring is unsubstituted or partially or fully substituted with same or different halogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, which groups are unsubstituted, or partially or fully substituted with same or different $R^8$, or phenyl which may be partially or fully substituted with $R^{11}$;

or $R^5$ and $R^6$, together with the nitrogen atom to which they are bound, form a 3-to 8-membered saturated, partially or fully unsaturated heterocyclic ring, which ring may contain 1, 2, 3, or 4 heteroatoms O, S, N, C=O and/or C=S as ring members, which heterocyclic ring is unsubstituted or partially or fully substituted with same or different halogen, CN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, which groups are unsubstituted, or partially or fully substituted with same or different $R^8$, or phenyl which may be partially or fully substituted with $R^{11}$;

or $R^5$ and $R^6$ together form a group =$C(R^8)_2$, =$S(O)_m(R^9)_2$, =$NR^{10a}$, or =$NOR^9$;

$R^{7a}$, $R^{7b}$ are each independently H, halogen, CN, $C_1$-$C_6$-alkyl, $C_3$-$C_8$-cycloalkyl, $C_2$-$C_6$-alkenyl, or $C_2$-$C_6$-alkynyl, which groups are unsubstituted, partially or fully halogenated and/or substituted with same or different $R^8$;

each $R^8$ is independently CN, $N_3$, $NO_2$, SCN, $SF_5$, $C_3$-$C_8$-cycloalkyl, $C_3$-$C_8$-halocycloalkyl, wherein the carbon chains may be substituted with one or more $R^{13}$;

$Si(R^{12})_3$, $OR^9$, $OSO_2R^9$, $S(O)_nR^9$, $N(R^{10a})R^{10b}$, $C(=O)N(R^{10a})R^{10b}$, $C(=S)N(R^{10a})R^{10b}$, $C(=O)R^9$, $CH=NOR^9$, phenyl, which is unsubstituted or partially or fully substituted with same or different $R^{16}$, or a 3-, 4-, 5-, 6- or 7-membered saturated, partially or fully unsaturated heterocyclic ring comprising 1, 2 or 3 heteroatoms N, O, and/or S as ring members, which ring is unsubstituted or partially or fully substituted with same or different $R^{16}$, or two $R^8$ present on the same carbon atom of an alkyl, alkenyl, alkynyl or cycloalkyl group together form a group =O, =$C(R^{13})_2$; =S; =$S(O)_m(R^{15})_2$, =$S(O)_mR^{15}N(R^{14a})R^{14b}$, =$NR^{10a}$, =$NOR^9$; or =$NN(R^{10a})R^{10b}$; or two radicals $R^8$, together with the carbon atoms of the alkyl, alkenyl, alkynyl or cycloalkyl group which they are bonded to, form a 3-, 4-, 5-, 6-, 7- or 8-membered saturated or partially unsaturated carbocyclic or heterocyclic ring, which heterocyclic ring comprises 1, 2, 3 or 4 heteroatoms N, O, and/or S as ring members, and which ring is unsubstituted, or partially or fully substituted with same or different $R^{16}$; and $R^8$ as a substituent on a cycloalkyl ring may additionally be $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, and $C_2$-$C_6$-haloalkynyl, which groups are unsubstituted, or partially or fully substituted with same or different $R^{13}$; and $R^8$ in the groups $C(=O)R^8$ and =$C(R^8)_2$ may additionally be H, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, or $C_2$-$C_6$-haloalkynyl, which groups are unsubstituted, or partially or fully substituted with same or different $R^{13}$;

each $R^9$ is independently H, CN, $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl-, $C_3$-$C_8$-halocycloalkyl, $C_2$-$C_6$-alkenyl, $C_2$-$C_6$-haloalkenyl, $C_2$-$C_6$-alkynyl, or $C_2$-$C_6$-haloalkynyl, which groups are unsubstituted, or partially or fully substituted with same or different $R^{13}$, or $C_1$-$C_6$-alkyl-$C(=O)OR^{15}$, $C_1$-$C_6$-alkyl-$C(=O)N(R^{14a})R^{14b}$, $C_1$-$C_6$-alkyl-$C(=S)N(R^{14a})R^{14b}$, $C_1$-$C_6$-alkyl-$C(=NR^{14})N(R^{14a})R^{14b}$, $Si(R^{12})_3$, $S(O)_nR^{15}$, $S(O)_nN(R^{14a})R^{14b}$, $N(R^{10a})R^{10b}$, $N=C(R^{13})_2$, $C(=O)R^{13}$, $C(=O)N(R^{14a})R^{14b}$, $C(=S)N(R^{14a})R^{14b}$, $C(=O)OR^{15}$, or phenyl, which is unsubstituted, or partially or fully substituted with $R^{16}$; and a 3- to 7-membered saturated, partially or fully unsaturated heterocyclic ring comprising 1, 2 or 3 heteroatoms N, O, and/or S as ring members, which ring is unsubstituted, or partially or fully substituted with same or different $R^{16}$; and $R^9$ in the groups $S(O)_nR^9$ and $OSO_2R^9$ may additionally be $C_1$-$C_6$-alkoxy, or $C_1$-$C_6$-haloalkoxy;

$R^{10a}$, $R^{10b}$ are independently from one another H, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, which groups are unsubstituted, or partially or fully substituted with same or different $R^{13}$;

$C_1$-$C_6$-alkyl-C(=O)OR$^{15}$, $C_1$-$C_6$-alkyl-C(=O)N(R$^{14a}$)R$^{14b}$, $C_1$-$C_6$-alkyl-C(=S)N(R$^{14a}$)R$^{14b}$, $C_1$-$C_6$-alkyl-C(=NR$^{14}$)N(R$^{14a}$)R$^{14b}$, $C_1$-$C_6$-alkoxy, $C_1$-$C_6$-haloalkoxy, $C_1$-$C_6$-alkylthio, $C_1$-$C_6$-haloalkylthio, $S(O)_nR^{15}$, $S(O)_nN(R^{14a})R^{14b}$, $C$(=O)$R^{13}$,
$C$(=O)OR$^{15}$, $C$(=O)N(R$^{14a}$)R$^{14b}$,
$C$(=S)$R^{13}$, $C$(=S)SR$^{15}$, $C$(=S)N(R$^{14a}$)R$^{14b}$, $C$(=NR$^{14}$)R$^{13}$;

phenyl, which is unsubstituted, or partially or fully substituted with same or different $R^{16}$; and a 3-, 4-, 5-, 6- or 7-membered saturated, partially or fully unsaturated heterocyclic ring comprising 1, 2, 3 or 4 heteroatoms N, O, and/or S as ring members, which ring is unsubstituted, or partially or fully substituted with same or different $R^{16}$; or $R^{10a}$ and $R^{10b}$ together with the nitrogen atom they are bonded to form a 3- to 8-membered saturated, partially or fully unsaturated heterocyclic ring, which ring may additionally contain one or two heteroatoms N, O, and/or S as ring members, which ring is unsubstituted, or partially or fully substituted with same or different halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be partially or fully substituted with $R^{16}$, and a 3-, 4-, 5-, 6-, or 7-membered saturated, partially or fully unsaturated heterocyclic ring comprising 1, 2 or 3 heteroatoms N, O, and/or S as ring members, which ring is unsubstituted, or partially or fully substituted with same or different $R^{16}$; or $R^{10a}$ and $R^{10b}$ together form a group =C(R$^{13}$)$_2$, =S(O)$_m$(R$^{15}$)$_2$, =S(O)$_m$R$^{15}$N(R$^{14a}$)R$^{14b}$, =NR$^{14}$, or =NOR$^{15}$;

$R^{11}$ is halogen, CN, N$_3$, NO$_2$, SCN, SF$_5$, $C_1$-$C_{10}$-alkyl, $C_3$-$C_8$-cycloalkyl, $C_2$-$C_{10}$-alkenyl, $C_2$-$C_{10}$-alkynyl, which groups are unsubstituted, partially or fully halogenated, and/or may be substituted with same or different $R^8$, or OR$^9$, NR$^{10a}$R$^{10b}$, S(O)$_n$R$^9$, Si(R$^{12}$)$_3$;

phenyl, which is unsubstituted, or partially or fully substituted with same or different $R^{16}$; and a 3- to 7-membered saturated, partially or fully unsaturated aromatic heterocyclic ring comprising 1, 2, 3, or 4 heteroatoms N, O, and/or S as ring members, which ring is unsubstituted, or partially or fully substituted with same or different $R^{16}$; or two $R^{11}$ present on the same ring carbon atom of an unsaturated or partially unsaturated heterocyclic ring may together form a group =O, =C(R$^{13}$)$_2$, =S, =S(O)$_m$(R$^{15}$)$_2$, =S(O)$_m$R$^{15}$N(R$^{14a}$)R$^{14b}$, =NR$^{14}$, =NOR$^{15}$, or =NN(R$^{14a}$)R$^{14b}$;

or two $R^{11}$ bound on adjacent ring atoms form together with the ring atoms to which they are bound a saturated 3- to 9-membered ring, which ring may contain 1 or 2 heteroatoms O, S, N, and/or NR$^{14}$, and/or 1 or 2 groups C=O, C=S, C=NR$^{14}$ as ring members, and which ring is unsubstituted, or partially or fully substituted with same or different halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be partially or fully substituted with same or different $R^{16}$, and a 3- to 7-membered saturated, partially or fully unsaturated heterocyclic ring containing 1, 2, or 3 heteroatoms N, O, and/or S as ring members, which ring is unsubstituted, or partially or fully substituted with same or different $R^{16}$;

each $R^{12}$ is independently $C_1$-$C_4$-alkyl and phenyl, which is unsubstituted, or partially or fully substituted with same or different $C_1$-$C_4$-alkyl;

each $R^{13}$ is independently CN, NO$_2$, OH, SH, SCN, SF$_5$, $C_1$-$C_6$-alkoxy, $C_1$-$C_6$-haloalkoxy, SO$_n$—$C_1$-$C_6$-alkyl, SO$_n$—$C_1$-$C_6$-haloalkyl, Si(R$^{12}$)$_3$, —C(=O)N(R$^{14a}$)R$^{14b}$, $C_3$-$C_8$-cycloalkyl which is unsubstituted, partially or fully halogenated or substituted with 1 or 2 same or different $C_1$-$C_4$-alkyl, $C_3$-$C_4$-cycloalkyl, $C_1$-$C_4$-alkoxy, $C_1$-$C_4$-haloalkoxy and/or oxo; phenyl, benzyl, phenoxy, where the phenyl moiety may be substituted with one or more same or different $R^{16}$; and a 3- to 7-membered saturated, partially or fully unsaturated heterocyclic ring containing 1, 2, or 3 heteroatoms N, O, and/or S, as ring members, which ring is unsubstituted, or partially or fully substituted with same or different $R^{16}$; or two $R^{13}$ present on the same carbon atom of an alkyl, alkenyl, alkynyl or cycloalkyl group may together be =O, =CH(C$_1$-$C_4$-alkyl), =C(C$_1$-$C_4$-alkyl)C$_1$-$C_4$-alkyl, =N(C$_1$-$C_6$-alkyl) or =NO(C$_1$-$C_6$-alkyl); and $R^{13}$ as a substituent of a cycloalkyl ring may additionally be $C_1$-$C_6$-alkyl, $C_2$-$C_6$-alkenyl or $C_2$-$C_6$-alkynyl, which groups are unsubstituted, partially or fully halogenated, or substituted with 1 or 2 CN, $C_3$-$C_4$-cycloalkyl, $C_1$-$C_4$-alkoxy, $C_1$-$C_4$-haloalkoxy, and oxo; and $R^{13}$ in groups =C(R$^{13}$)$_2$, N=C(R$^{13}$)$_2$, C(=O)R$^{13}$, C(=S)R$^{13}$, and C(=NR$^{14}$)R$^{13}$ may additionally be H, halogen, $C_1$-$C_6$-alkyl, $C_2$-$C_6$-alkenyl, or $C_2$-$C_6$-alkynyl, which groups are unsubstituted, partially or fully halogenated, or substituted with 1 or 2 CN, $C_3$-$C_4$-cycloalkyl, $C_1$-$C_4$-alkoxy, $C_1$-$C_4$-haloalkoxy, and oxo;

each $R^{14}$ is independently H, CN, $C_1$-$C_6$-alkoxy, $C_1$-$C_6$-haloalkoxy, SO$_n$—$C_1$-$C_6$-alkyl, SO$_n$—$C_1$-$C_6$-haloalkyl, Si(R$^{12}$)$_3$;

$C_1$-$C_6$-alkyl, $C_2$-$C_6$-alkenyl, $C_2$-$C_6$-alkynyl, which groups are unsubstituted, partially or fully halogenated, or substituted with 1 or 2 CN, $C_1$-$C_4$-alkoxy, $C_1$-$C_4$-haloalkoxy, SO$_n$—$C_1$-$C_4$-alkyl, $C_3$-$C_6$-cycloalkyl which is unsubstituted or substituted with 1 or 2 substituents halogen and CN; and oxo;

$C_3$-$C_8$-cycloalkyl which is unsubstituted, or partially or fully halogenated or substituted with 1 or 2 CN, $C_1$-$C_4$-alkyl, $C_1$-$C_4$-alkoxy, $C_1$-$C_4$-haloalkoxy, SO$_n$—$C_1$-$C_6$-alkyl, $C_3$-$C_4$-cycloalkyl, $C_3$-$C_4$-cycloalkyl-$C_1$-$C_4$-alkyl-, which groups are unsubstituted, or substituted with 1 or 2 substituents selected from halogen and CN;

phenyl, benzyl, pyridyl, phenoxy, which cyclic moieties are unsubstituted, or substituted with one or more same or different halogen, CN, NO$_2$, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_2$-C$_4$-alkenyl, C$_2$-C$_4$-haloalkenyl, C$_2$-C$_4$-alkynyl, C$_2$-C$_4$-haloalkynyl, C$_3$-C$_6$-cycloalkyl, C$_3$-C$_6$-halocycloalkyl, and C$_1$-C$_6$-alkoxycarbonyl;

and a 3-, 4-, 5- or 6-membered saturated, partially or fully unsaturated heterocyclic ring comprising 1, 2 or 3 heteroatoms N, O, and/or S as ring members, which ring is unsubstituted, or partially or fully substituted with same or different R$^{16}$;

R$^{14a}$ and R$^{14b}$ independently of each other, have one of the meanings given for R$^{14}$; or R$^{14a}$ and R$^{14b}$, together with the nitrogen atom to which they are bound, form a 3- to 7-membered saturated, partially, or fully unsaturated heterocyclic ring, wherein the ring may additionally contain 1 or 2 heteroatoms N, O, and/or S as ring members, which ring is unsubstituted, or partially or fully substituted with same or different halogen, C$_1$-C$_4$-alkyl, C$_1$-C$_4$-haloalkyl, C$_1$-C$_4$-alkoxy, or C$_1$-C$_4$-haloalkoxy; or R$^{14a}$ and R$^{14}$ or R$^{14b}$ and R$^{14}$, together with the nitrogen atoms to which they are bound in the group C(=NR$^{14}$)N(R$^{14a}$)R$^{14b}$, form a 3- to 7-membered partially, or fully unsaturated heterocyclic ring, wherein the ring may additionally contain 1 or 2 heteroatoms N, O, and/or S as ring members, which ring is unsubstituted, or partially or fully substituted with same or different halogen, C$_1$-C$_4$-haloalkyl, C$_1$-C$_4$-alkoxy, or C$_1$-C$_4$-haloalkoxy;

each R$^{15}$ is independently H, CN, Si(R$^{12}$)3 C$_1$-C$_6$-alkyl, C$_2$-C$_6$-alkenyl, C$_2$-C$_6$-alkynyl, which groups are unsubstituted, partially or fully halogenated, or substituted with 1 or 2 radicals C$_3$-C$_4$-cycloalkyl, C$_1$-C$_4$-alkoxy, C$_1$-C$_4$-haloalkoxy, SO$_n$—C$_1$-C$_6$-alkyl, or oxo;

C$_3$-C$_8$-cycloalkyl which is unsubstituted, partially or fully halogenated or substituted with 1 or 2 radicals C$_1$-C$_4$-alkyl, C$_3$-C$_4$-cycloalkyl, C$_1$-C$_4$-alkoxy, C$_1$-C$_4$-haloalkoxy, SO$_n$—C$_1$-C$_6$-alkyl, or oxo;

phenyl, benzyl, pyridyl, and phenoxy, which rings are unsubstituted, partially or fully halogenated, or substituted with 1, 2 or 3 substituents C$_1$-C$_6$-alkyl, C$_1$-C$_6$-haloalkyl, C$_1$-C$_6$-alkoxy, C$_1$-C$_6$-haloalkoxy, or (C$_1$-C$_6$-alkoxy)carbonyl;

each R$^{16}$ is independently halogen, NO$_2$, CN, OH, SH, C$_1$-C$_6$-alkoxy, C$_1$-C$_6$-haloalkoxy, SO$_n$—C$_1$-C$_6$-alkyl, SO$_n$—C$_1$-C$_6$-haloalkyl, C$_1$-C$_4$-alkylcarbonyl, C$_1$-C$_4$-haloalkylcarbonyl, C$_1$-C$_4$-alkoxycarbonyl, C$_1$-C$_4$-haloalkoxycarbonyl, aminocarbonyl, C$_1$-C$_4$-alkylaminocarbonyl, di-(C$_1$-C$_4$-alkyl)-aminocarbonyl, Si(R$^{12}$)$_3$;

C$_1$-C$_6$-alkyl, C$_2$-C$_6$-alkenyl, C$_2$-C$_6$-alkynyl, which groups are unsubstituted, partially or fully halogenated, or substituted with 1 or 2 radicals CN, C$_3$-C$_4$-cycloalkyl, C$_1$-C$_4$-alkoxy, C$_1$-C$_4$-haloalkoxy, or oxo;

C$_3$-C$_8$-cycloalkyl which is unsubstituted, partially or fully halogenated or substituted with 1 or 2 radicals CN, C$_1$-C$_4$-alkyl, C$_3$-C$_4$-cycloalkyl, C$_1$-C$_4$-alkoxy, C$_1$-C$_4$-haloalkoxy, or oxo;

phenyl, benzyl, pyridyl and phenoxy, which rings are unsubstituted, partially or fully halogenated, or substituted with 1, 2 or 3 substituents C$_1$-C$_6$-alkyl, C$_1$-C$_6$-haloalkyl, C$_1$-C$_6$-alkoxy, C$_1$-C$_6$-haloalkoxy, or (C$_1$-C$_6$-alkoxy)carbonyl; or two R$^{16}$ present together on the same atom of an unsaturated or partially unsaturated ring may be =O, =S, =N(C$_1$-C$_6$-alkyl), =NO—C$_1$-C$_6$-alkyl, =CH(C$_1$-C$_4$-alkyl), or =C(C$_1$-C$_4$-alkyl)$_2$; or two R$^{16}$ on two adjacent carbon atoms form together with the carbon atoms they are bonded to a 4- to 8-membered saturated, partially or fully unsaturated ring, wherein the ring may contain 1 or 2 heteroatoms N, O, and/or S as ring members, which ring is unsubstituted, or partially or fully substituted with same or different halogen, C$_1$-C$_4$-alkyl, C$_1$-C$_4$-haloalkyl, C$_1$-C$_4$-alkoxy, or C$_1$-C$_4$-haloalkoxy;

each m is independently 0, or 1;

comprising preparing 5-bromo-1,3-dichloro-2-fluorobenzene according to claim 1, further transforming it to VI,

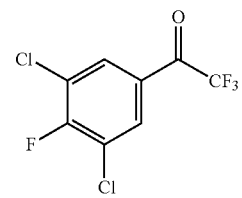

reacting VI to VII,

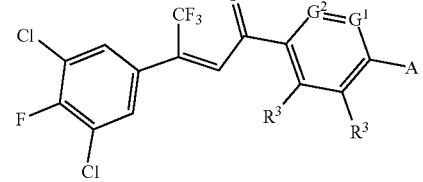

and cyclizing VII to yield V.

11. The process of claim 10, wherein the formula V corresponds to formula V.A

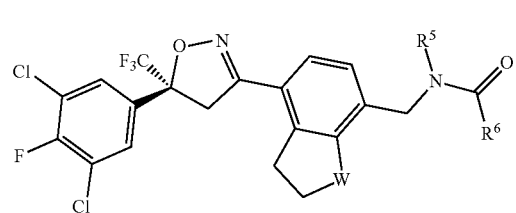

wherein W is CH or O, R$^5$ is H or CH$_3$, and R$^6$ is H, C$_1$-C$_6$-alkyl, or C$_2$-C$_6$-alkenyl.

12. The process of claim 10, wherein the formula V corresponds to formula V.B

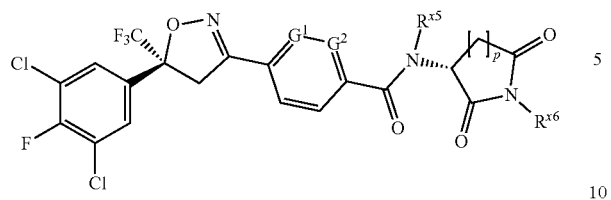
V.B
wherein $G^1$ is CH, and $G^2$ is $CR^3$; wherein $R^3$ is halogen, or $C_1$-$C_2$-alkyl; p is 1 or 2; $R^{x5}$ is H or $CH_3$, and $R^{x6}$ is $CH_3$, $C_2H_5$, $CH_2(CH_3)_2$, $CH_2CH\!\!=\!\!CH_2$, $CH_2CF_3$, $CH_2CH_2CF_3$, $CH_2C_6H_5$, or $CH_2C(\!\!=\!\!O)OCH_3$.
\* \* \* \* \*